US00PP09632P

United States Patent [19]

Trees

[11] Patent Number: Plant 9,632

[45] Date of Patent: Aug. 20, 1996

[54] POINSETTIA PLANT NAMED 'RED SPLENDOR'

[75] Inventor: Scott C. Trees, Arroyo Grande, Calif.

[73] Assignee: Geo. J. Ball, Inc., West Chicago, Ill.

[21] Appl. No.: 422,692

[22] Filed: Apr. 14, 1995

[51] Int. Cl.[6] ..... A01H 5/00

[52] U.S. Cl. ..... Plt./86.4

[58] Field of Search ..... Plt./86.4

*Primary Examiner*—James R. Feyrer

*Attorney, Agent, or Firm*—Burns, Doane, Swecker & Mathis, L.L.P.

[57] ABSTRACT

A new and distinct *Euphorbia pulcherrima* cultivar named 'Red Splendor' is provided which exhibits attractive generally clear Currant Red bracts and dark green foliage. This new cultivar exhibits a midseason finishing time and was the product of a planned breeding program combined with phenotypical transformation following grafting. The bracts commonly are upwardly disposed and present to the viewer a vigorous display of coloration. The overall growth habit is the product of strong basal branching to form a very compact plant that is amenable for display in a wide variety of settings. Sturdy thick stems are also a characteristic of the new cultivar.

1 Drawing Sheet

SUMMARY OF THE INVENTION

The present invention concerns a new and distinct Ponsettia cultivar, botanically known as *Euphorbia pulcherrima*, and hereinafter is referred to by the cultivar name 'Red Splendor'.

The new cultivar is the product of a planned breeding program that was combined with phenotypical transformation to create an attractive new Poinsettia cultivar having dark red bracts and a mid-season finishing time.

More specifically, the new cultivar was created during 1991 at Arroyo Grande, Calif., U.S.A., through the creation, selection, and grafting of a specific Poinsettia scion cultivar onto a specific Poinsettia rootstock cultivar which yielded the new cultivar of the present invention following the transformation of the scion cultivar. The scion cultivar was designated 328-6 and originated as a seedling resulting by the cross of a proprietary seedling of Ball FloraPlant having dark red bracts and medium green foliage designated BSR-33 as the female parent and the 'Lilo' cultivar (U.S. Plant Pat. No. 6,694) having dark red bracts and dark green foliage as the male parent. The 328-6 scion was next grafted onto a rootstock of the 'Supjibi' cultivar (U.S. Plant Pat. No. 6,592) which served to induce significant self-branching and the exhibition of a slightly lesser level of bright red coloration in the bracts.

The utilization of grafting to bring about some types of transformation is discussed in (1) J. Amer. Soc. Hort. Sci. 108: 419–422 (1983) entitled "Promotion and Inhibition of Branching in Poinsettia in Grafts Between Self-Branching and Nonbranching Cultivars" by D. P. Stimart, (2) U.S. Pat. No. 4,724,276 to P. Ecke, Jr., and (3) J. Amer. Hort. Soc. Sci. 116(2): 307–311 (1991) entitled "Vegetative and Reproductive Characteristics of Poinsettia Altered by A Graft-Transmissible Agent" by J. M. Dole and H. F. Wilkins.

The initial selection following approach grafting was made during June, 1992, and asexual propagation was first carried out in a controlled environment during 1992 through the use of vegetative cuttings at Arroyo Grande, Calif., U.S.A. This selection was initially designated BFP-633. A more detailed horticultural examination of the selected plant was initiated at Arroyo Grande, Calif., U.S.A. during August, 1993, and has confirmed that the novel combination of characteristics of the new 'Red Splendor' cultivar is firmly fixed and is retained following successive generations of asexual reproduction through the use of vegetative cuttings.

It was found that the new Poinsettia cultivar of the present invention:

(a) exhibits under natural short days a response period to initiate bract coloration of approximately 9 to 10 weeks when grown in central California,
(b) forms attractive clear red bracts that are commonly upwardly disposed,
(c) forms dark green foliage that creates an attractive contrast with the bract coloration,
(d) forms sturdy thick stems, and
(e) exhibits a strong basal branching character with pinching to create a very compact growth habit.

The bracts tend to exhibit an uncommon uniformity in size, color and placement, and are sufficiently imbricated to substantially overwhelm but yet pleasantly contrast with the foliage. The bract size reduction from large to small tends to be somewhat uniform resulting in an arranged appearance of the bracts around a well-centered cyathia grouping on each bract.

The thickness of the sturdy stems of the new cultivar commonly exeeds that of other representative cultivars, such as 'Freedom' (non-patented in the United States), 'Lilo' (U.S. Plant Pat. No. 6,694) and 'BFP-437G' (U.S. Plant Pat. No. 8,250). More specifically, when plants are grown in 6 inch pots, a comparison of stem thickness can be made by observing the top three branches between the third and fourth nodes of each branch 10 weeks after the start of a short day period which followed a long day period of 4 weeks. It was found that the new cultivar of the present invention commonly exhibits an average stem diameter of approximately 5.5 mm. when measured as described. This can be compared to average stem diameters of approximately 4.2 mm. for the 'Freedom' cultivar, approximately 3.9 mm. for the 'Lilo' cultivar, and approximately 4.0 mm. for the 'BFP-437G' cultivar.

As illustrated, a simultaneous exhibition of red and green sometimes is visible on transition bracts with the green often being present at venation. A midseason finishing time is observed, and the plant performs well in the absence of a growth regulator.

The 'Red Splendor' cultivar has not been observed under all possible environmental conditions to date. Accordingly, it is possible that the phenotype may vary somewhat with variations in the environment, such as temperature, light intensity and day length.

BRIEF DESCRIPTION OF THE PHOTOGRAPH

The accompanying photograph of FIG. 1 shows as nearly true as it is reasonably possible to make the same in a color illustration of this character, a typical specimen of the new cultivar. The depicted container holds only one specimen. The overall growth habit is illustrated.

DETAILED DESCRIPTION

Figure 1:
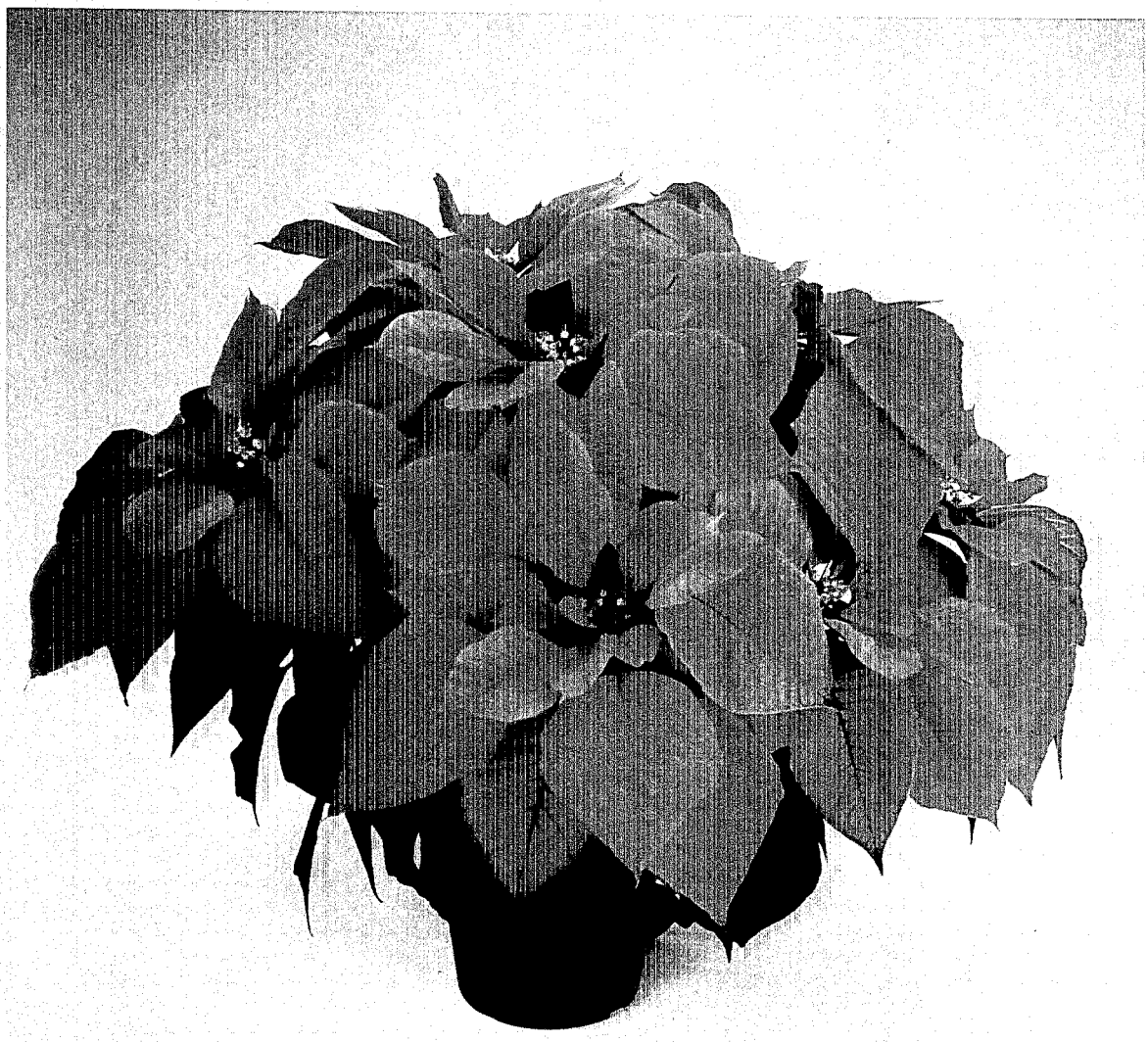

The chart used in the identification of colors described herein is the R.H.S. Colour Chart of The Royal Horticultural Society, London, England. The color values were determined on Dec. 13, 1994 using a light intensity of 4,000 footcandles at West Chicago, Ill., U.S.A. The plants described were grown under standard greenhouse conditions.

Classification:

*Botanical.*—*Euphorbia pulcherrima.*

*Commercial.*—Poinsettia.

*Cultivar name.*—'Red Splendor'

Parentage:

*Scion parent.*—328-6 seedling that was formed by the cross of a proprietary seedling designated BSR-33 as female parent and the 'Lilo' cultivar (U.S. Plant Pat. No. 6,694) as the male parent.

*Rootstock parent.*—'Supjibi' cultivar (U.S. Plant Pat. No. 6,592).

Plant:

*Form.*—Upright, and vase-shaped.

*Growth habit.*—Upright.

*Rooting.*—Well-rooted following approximately 14 to 21 days in OASIS-brand cubes.

*Blooming season.*—Under natural short days at West Chicago, Ill., U.S.A., from approximately December 1st to approximately January 15th.

*Blooming habit.*—Large oval-shaped bracts turning color in response to short days.

*Foliage size.*—Approximately 9.0 to 10.5 cm. in width and approximately 10.8 to 11.5 cm. in length.

*Foliage quantity.*—Approximately 7 to 10 leaves per flowering stem depending upon the culture experienced.

*Foliage color.*—New Foliage: Green Group 135A (adaxial) and Green Group 137B (abaxial). Old Foliage: slightly darker than Green Group 136A (adaxial) and Green Group 139A (abaxial) with petioles of Red Group 46B.

*Foliage configuration.*—The leaves are basically ovate, possess margins ranging from repand to slightly crenate, possess a variable leaf edge margin and a pointed tip.

*Foliage texture.*—Dull and display veins on upper and lower surfaces which approximate Yellow-Green Group 146C.

*Disease resistance.*—Some tolerance to powdery mildew.

Flowers:

*Borne.*—In a compound corymb.

*Reproductive organs.*—Approximately cyathia 11 to 12 per stem when the plant is in full bloom. Each cyanthium is approximately 5 to 8 mm. in lengh, approximately 5 to 6 mm. in width, and is green fringed with red coloration at the distal end. A yellow nectar cup protrudes from the side of each cyanthium and commonly exudes nectar in an abundant quantity.

*Bract color.*—Currant Red, Red Group 46A on the upper side, and approaching Cardinal Red, Red Group 53C, on the under side.

*Bract size.*—Larger lower bracts are approximately 11.4 cm. in width and approximately 12 to 14 cm. in length, and the smaller upper bracts are approximately 4 cm. in length and approximately 1.8 cm. in width. The petioles are approximately 5 to 6 cm. in length.

*Pedicel.*—Approximately 3 to 5 mm. in length and green in coloration.

*Stamens.*—Protrude from cyathia and are reddish in coloration.

*Pollen.*—Commonly present in an abundant quantity and yellow in coloration.

*Fertility.*—No seeds have been observed to date following extensive attempts at self-pollination and cross-pollination.

I claim:

1. A new and distinct cultivar of Poinsettia plant named 'Red Splendor' substantially as herein shown and described, which:

(a) exhibits under natural short days a response period to initiate bract coloration of approximately 9 to 10 weeks when grown in central California, (b) forms attractive clear red bracts that are commonly upwardly disposed, (c) forms dark green foliage that creates an attractive contrast with the bract coloration, (d) forms sturdy thick stems, and (e) exhibits a strong basal branching character with pinching to create a very compact growth habit.

* * * * *